(12) United States Patent
Gross (10) Patent No.: US 7,544,160 B2
(45) Date of Patent: Jun. 9, 2009

(54) EXTRACARDIAC BLOOD FLOW AMPLIFICATION DEVICE

(76) Inventor: Yossi Gross, 10 HaNotea Street, Moshav Mazor 73160 (IL)

( * ) Notice: Subject to any disclaimer, the term of this patent is extended or adjusted under 35 U.S.C. 154(b) by 302 days.

(21) Appl. No.: 11/349,062

(22) Filed: Feb. 7, 2006

(65) Prior Publication Data
US 2006/0178552 A1 Aug. 10, 2006

Related U.S. Application Data

(60) Provisional application No. 60/651,751, filed on Feb. 10, 2005.

(51) Int. Cl.
*A61M 1/12* (2006.01)
*A61M 5/14* (2006.01)

(52) U.S. Cl. .................. 600/16; 604/8; 604/19

(58) Field of Classification Search ............ 128/200.24; 417/423.1; 600/16; 604/151; 623/3.14, 623/3.21
See application file for complete search history.

(56) References Cited

U.S. PATENT DOCUMENTS

| | | | |
|---|---|---|---|
| 4,527,549 A | 7/1985 | Gabbay | |
| 4,583,523 A | 4/1986 | Kleinke et al. | |
| 4,753,221 A * | 6/1988 | Kensey et al. | 600/16 |
| 4,809,676 A | 3/1989 | Freeman | |
| 4,919,647 A * | 4/1990 | Nash | 600/16 |
| 4,938,766 A | 7/1990 | Jarvik | |
| 5,324,177 A * | 6/1994 | Golding et al. | 417/423.1 |
| 5,749,855 A * | 5/1998 | Reitan | 604/151 |
| 5,928,132 A * | 7/1999 | Leschinsky | 600/16 |
| 6,030,336 A | 2/2000 | Franchi | |
| 6,083,260 A * | 7/2000 | Aboul-Hosn | 623/3.14 |
| 6,168,624 B1 * | 1/2001 | Sudai | 623/3.21 |
| 6,245,007 B1 * | 6/2001 | Bedingham et al. | 600/16 |
| 6,299,575 B1 | 10/2001 | Bolling | |
| 6,387,037 B1 | 5/2002 | Bolling et al. | |
| 6,450,942 B1 | 9/2002 | Lapanshvili et al. | |
| 6,572,652 B2 | 6/2003 | Shaknovich | |
| 6,730,118 B2 | 5/2004 | Spenser et al. | |
| 2002/0103413 A1 | 8/2002 | Bugge et al. | |

(Continued)

OTHER PUBLICATIONS

Clauses, et al., "Assisted Circulation: 1. The Arterial Counterpulsator", Journal of Thoracic and Cardiovascular Surgery, 41:447, Apr. 1961.

(Continued)

*Primary Examiner*—Carl H Layno
*Assistant Examiner*—Luther G Behringer
(74) *Attorney, Agent, or Firm*—Ladas and Parry LLP (57) ABSTRACT

Apparatus is provided including an element shaped so as to define at least one surface. The element is adapted to be implanted in an ascending aorta of a subject in a vicinity of an aortic valve, and, during systole, to store, as potential energy, work applied to the surface by blood of the subject passing through the element. The element allows at least 75% of the blood passing into the element during systole of each cardiac cycle to exit the element during systole of the respective cardiac cycle. The element applies the stored energy to push blood towards at least one coronary artery of the subject during diastole. For some applications, the surface includes a first surface, and the element is shaped so as to define a second surface, which is configured to apply the stored energy. Other embodiments are also described.

9 Claims, 12 Drawing Sheets

U.S. PATENT DOCUMENTS

2003/0127090 A1* 7/2003 Gifford et al. .......... 128/200.24
2003/0135086 A1* 7/2003 Khaw et al. ................... 600/16
2004/0097783 A1* 5/2004 Peters et al. .................. 600/16
2004/0116769 A1 6/2004 Jassawalla et al.
2005/0103340 A1 5/2005 Wondka
2005/0159640 A1* 7/2005 Barbut et al. .................. 600/16
2006/0122456 A1* 6/2006 LaRose et al. ................ 600/16
2006/0195004 A1* 8/2006 Jarvik ......................... 600/16

OTHER PUBLICATIONS

G. Gregoratos, et al., "ACC/AHA/NASPE 2002 Practice Guidelines", JACC vol. 40, No. 9, 2002, Nov. 6, 2002, 1703-19.

F. Unger, et al., "The Windkesselventricle with guiding balloon as a new approach for assisted circulation", Medical Instrumentation, vol. 10, No. 5, Sep.-Oct. 1976.

W.C. Birtwell, et al., "The evoloution of counterpulsation techniques", Medical Instrumentation, vol. 10, No. 5, Sep.-Oct. 1976.

* cited by examiner

EXTRACARDIAC BLOOD FLOW AMPLIFICATION DEVICE

CROSS-REFERENCES TO RELATED APPLICATIONS

This application claims the benefit of U.S. Provisional Patent Application 60/651,751 to Gross, filed Feb. 10, 2005, which is incorporated herein by reference.

FIELD OF THE INVENTION

The present invention relates generally to implantable medical devices, and specifically to methods and apparatus for implantable devices for treating conditions caused by insufficient blood circulation.

BACKGROUND OF THE INVENTION

Numerous medical conditions are caused by insufficient blood flow to certain tissues. For example, angina and myocardial infarction are caused by insufficient blood flow to cardiac muscle, and ischemic stroke is caused by insufficient blood flow to the brain.

US Patent Application Publication 2002/0103413 to Bugge et al., which is incorporated herein by reference, describes an implanted device for utilizing at least a part of the hydraulic energy generated by the heart to power various apparatus. The device typically includes a hydraulic motor powered by pressurized blood, which converts hydraulic energy into mechanical or electrical energy. The device typically stores the energy, and uses the stored energy to power an executing device, such as a pump or an electric motor. For some applications, the hydraulic motor is connected directly to one or more ventricles of the heart. Numerous embodiments of the device are described.

U.S. Pat. No. 4,527,549 to Gabbay, which is incorporated herein by reference, describes techniques for providing improved cardiac assist by the use of a intraaortic balloon. A single small balloon is placed in the ascending aorta close to the aortic valve, such placement being described as effective for producing a substantially stronger augmentation of heart action than with the use of a longer balloon normally placed, for example, in the descending aorta. Multiple small balloons positioned in the aortic arch, with or without a large balloon in the descending aorta, can be used to provide even stronger coronary flows.

U.S. Pat. No. 6,730,118 to Spenser et al., which is incorporated herein by reference, describes a valve prosthesis device suitable for implantation in body ducts. The device comprises a support stent, comprised of a deployable construction adapted to be initially crimped in a narrow configuration suitable for catheterization through the body duct to a target location and adapted to be deployed by exerting substantially radial forces from within by means of a deployment device to a deployed state in the target location, and a valve assembly comprising a flexible conduit having an inlet end and an outlet, made of pliant material attached to the support beams providing collapsible slack portions of the conduit at the outlet. The support stent is provided with a plurality of longitudinally rigid support beams of fixed length. When flow is allowed to pass through the valve prosthesis device from the inlet to the outlet, the valve assembly is kept in an open position, whereas a reverse flow is prevented as the collapsible slack portions of the valve assembly collapse inwardly providing blockage to the reverse flow.

SUMMARY OF THE INVENTION

In some embodiments of the present invention, an extracardiac fully-implantable blood flow amplification device is provided for amplifying blood flow to the coronary arteries. The device is typically adapted to be implanted in an ascending aorta in a vicinity of an aortic valve. The device is configured to store, as potential energy, work applied to a surface of the device by blood flowing through the device during systole. During diastole, the device applies the stored energy to push blood into the cardiac arteries, thereby increasing blood pressure and flow in the coronary arteries. The device typically does not comprise a power supply for powering the device's blood flow amplification.

In some embodiments of the present invention, the amplification device is configured to allow a substantial portion of blood (e.g., at least 25%, 50%, or 75% of the blood) entering the device each cardiac cycle to pass through and exit the device during the respective cardiac cycle. Typically, blood passing through the device does not pass through any valves, and is not temporarily stored in any chamber. In other words, typically the device constantly allows the passage of blood therethrough.

In some embodiments of the present invention, the amplification device comprises a hollow longitudinal element and at least one elliptical (e.g., circular) flap, typically positioned near a distal end of the element (i.e., the end further downstream from the aortic valve). Blood passing through the element during systole applies work to a surface of the element, thereby longitudinally expanding the element and storing energy therein. As the element expands, the flap typically folds down against an external surface of the element because of resistance by blood in the aorta. During diastole, the energy stored in the element causes the element to contract longitudinally. During the contraction, blood in the aorta causes the flap to open away from the element, such that the open flap pushes blood into the coronary arteries, thereby increasing blood pressure and flow in the coronary arteries.

In some embodiments of the present invention, the amplification device comprises a generally helically-shaped spring or other elastic element, a diameter of which typically decreases from a proximal end towards a distal apex thereof. During systole, blood flows through the helical element, applying work to the element, thereby longitudinally expanding the element and storing energy therein. During diastole, the energy stored in the helical element causes the element to contract longitudinally. During the contraction, the element pushes blood towards and into the coronary arteries, thereby increasing blood pressure and flow in the coronary arteries.

In some embodiments of the present invention, the amplification device comprises a cylindrical casing, a turbine mounted in the casing, and an elastic element, such as a spring. For some applications, the elastic element comprises a spring having a planar spiral shape, similar to a mechanical watch spring. During systole, blood flows through the casing and the turbine, causing the turbine to rotate in a first direction. The rotation of the turbine applies work to the elastic element, thereby storing energy therein. During diastole, the energy stored in the elastic element causes the turbine to rotate in a second direction, opposite the first direction. This rotation causes blades of the turbine to push blood towards and into the coronary arteries, thereby increasing blood pressure and flow in the coronary arteries.

In some embodiments of the present invention, the amplification device comprises a generally dome-shaped elastic cup element, shaped so as to define an opening at a proximal end thereof (i.e., the end nearer the aortic valve). At a distal end thereof, the cup element comprises a valve. At the beginning of systole, the cup element is in its most contracted, resting position. During systole, blood enters the cup element, and applies work to the flexible wall of the cup element, causing the cup element to expand longitudinally and store energy in the wall thereof. As systole continues, the blood pressure in the cup element continues to increase, until a sufficient pressure gradient causes the valve to open, allowing blood to pass through the amplification device into the ascending aorta. As the blood pressure within the cup element drops during diastole, the valve closes, and the energy stored in the cup element causes the cup element to contract longitudinally. During the contraction, the cup element pushes blood towards and into the coronary arteries, thereby increasing blood pressure and flow in the coronary arteries.

In some embodiments of the present invention, an extracardiac fully-implantable blood flow amplification device is provided for amplifying blood flow to the coronary arteries. The device is adapted to be implanted in an ascending aorta in a vicinity of an aortic valve. The device is configured such that during systole, blood flows through the device (i.e., into and out of the device), applying work to a surface of the device. The device utilizes a portion of the applied work to increase blood flow to the coronary arteries during systole, thereby increasing blood pressure and flow in the coronary arteries. The device typically does not comprise a power supply for powering the device's blood flow amplification.

In some embodiments of the present invention, the amplification device comprises a cylindrical casing, a turbine mounted in the casing, and one or more lower elements, such as blades, coupled to a proximal end of the turbine (i.e., the end nearer the aortic valve). During systole, blood flows through the casing and the turbine, causing the turbine to rotate, thereby rotating the lower elements. The movement of the lower elements during systole pushes blood towards and into the coronary arteries, thereby increasing blood pressure and flow in the coronary arteries.

There is therefore provided, in accordance with an embodiment of the present invention, apparatus including an element shaped so as to define at least one surface, the element adapted to:
  be implanted in an ascending aorta of a subject in a vicinity of an aortic valve,
  during systole, store, as potential energy, work applied to the surface by blood of the subject passing through the element,
  allow at least 75% of the blood passing into the element during systole of each cardiac cycle to exit the element during systole of the respective cardiac cycle, and
  apply the stored energy to push blood towards at least one coronary artery of the subject during diastole.

In an embodiment, the surface includes a first surface, and the element is shaped so as to define a second surface, which is configured to apply the stored energy.

There is also provided, in accordance with an embodiment of the present invention, apparatus including an element shaped so as to define at least one surface, the element adapted to:
  be implanted in an ascending aorta of a subject in a vicinity of an aortic valve,
  during systole, store, as potential energy, work applied to the surface by blood of the subject passing through the element,
  constantly allow passage of blood therethrough, and
  apply the stored energy to push blood towards at least one coronary artery of the subject during diastole.

There is further provided, in accordance with an embodiment of the present invention, apparatus including an element shaped so as to define at least one surface, the element adapted to:
  be implanted in an ascending aorta of a subject in a vicinity of an aortic valve,
  during systole, push blood of the subject towards at least one coronary artery of the subject by using energy applied to the surface by blood of the subject passing through the element during systole, and
  allow at least 75% of the blood passing into the element during systole of each cardiac cycle to exit the element during systole of the respective cardiac cycle.

There is still further provided, in accordance with an embodiment of the present invention, apparatus adapted to be implanted in an ascending aorta of a subject in a vicinity of an aortic valve, the apparatus including:
  a hollow, flexible longitudinal element, shaped so as to define an interior surface that defines an interior region of the element that is in fluid communication with blood pumped through the aortic valve during systole, the element adapted to:
    store, as potential energy, energy applied to the interior surface by blood passing through the element during systole, and
    allow at least 75% of the blood passing into the element during systole of each cardiac cycle to exit the element during systole of the respective cardiac cycle; and
  an elliptical flap, coupled to the element, the flap adapted to apply the stored energy to push blood towards at least one coronary artery of the subject during diastole.

There is yet further provided, in accordance with an embodiment of the present invention, apparatus adapted to be implanted in an ascending aorta of a subject in a vicinity of an aortic valve, the apparatus including a helically-shaped elastic element, the element adapted to:
  store, as potential energy, energy applied to the element by the blood passing through the element during systole,
  allow at least 75% of the blood passing into the element during systole of each cardiac cycle to exit the element during systole of the respective cardiac cycle, and
  apply the stored energy to push blood towards at least one coronary artery during diastole.

There is also provided, in accordance with an embodiment of the present invention, apparatus adapted to be implanted in an ascending aorta of a subject in a vicinity of an aortic valve, the apparatus including:
  a turbine, including an axial shaft and one or more turbine blades coupled to the shaft, the turbine configured to rotate in a first direction when blood passing through the turbine during systole applies work to the blades; and
  an elastic element, coupled to the turbine, and adapted to:
    store energy generated by the rotation of the turbine in the first direction during systole, and
    during diastole, apply the stored energy to rotate the turbine in a second direction opposite the first direction, so as to drive the blades to push blood towards at least one coronary artery of the subject.

There is yet additionally provided, in accordance with an embodiment of the present invention, apparatus adapted to be implanted in an ascending aorta of a subject in a vicinity of an aortic valve, the apparatus including:
  a turbine, including an axial shaft and one or more turbine blades coupled to the shaft, the turbine configured to rotate when blood passing through the turbine during systole applies work to the blades; and one or more lower elements, coupled to a proximal end of the turbine, and configured to push blood towards at least one coronary artery of the subject during systole when rotated by the rotation of the turbine.

There is still additionally provided, in accordance with an embodiment of the present invention, apparatus adapted to be implanted in an ascending aorta of a subject in a vicinity of an aortic valve, the apparatus including a cup element, which includes an elastic wall, the cup element shaped so as to define an opening at a proximal end thereof, the cup element including, at a distal end thereof, a valve, the cup element adapted to expand longitudinally and store energy in the wall, as blood flows into the cup element during a first period of systole, the valve adapted to open during a second period of systole following the first period, and to close during a third period following the second period, and the cup element adapted to contract longitudinally during a fourth period of diastole following the third period, thereby pushing blood towards at least one coronary artery of the subject.

The present invention will be more fully understood from the following detailed description of embodiments thereof, taken together with the drawings, in which:

DETAILED DESCRIPTION OF EMBODIMENTS

Figure 1:
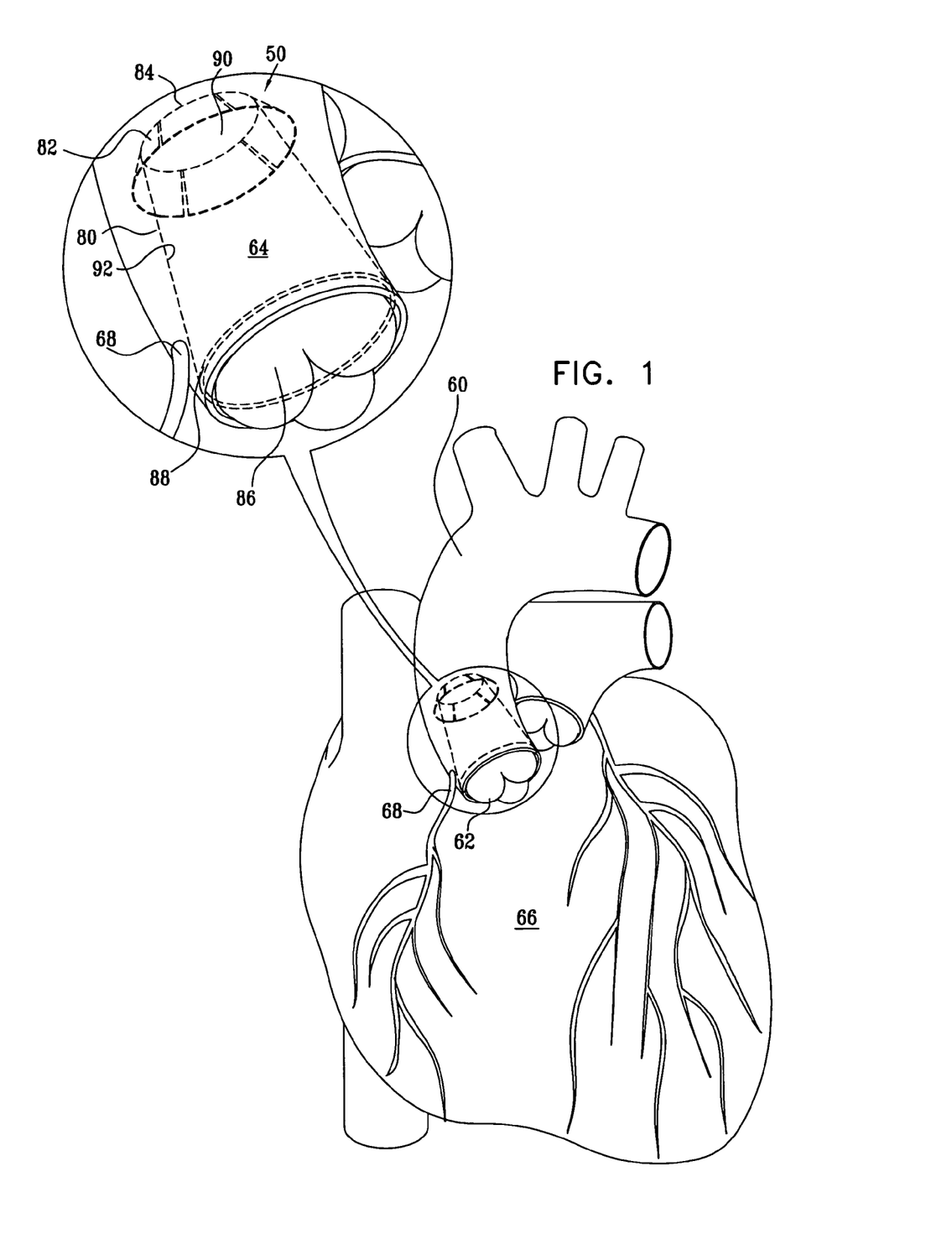
FIG. 1 is a schematic illustration of an extracardiac blood flow amplification device, in accordance with an embodiment of the present invention.

Reference is now made to FIG. 1, which is a schematic illustration of an extracardiac blood flow amplification device 50, in accordance with an embodiment of the present invention. Amplification device 50 is adapted to be implanted in an ascending aorta 60 in a vicinity of an aortic valve 62, typically such that a proximal end 88 of device 50 (i.e., the end nearer the aortic valve) is located between the aortic valve and the left and right coronary sinuses (from which branch the coronary arteries). An interior region 64 of amplification device 50 is in fluid communication with blood pumped from a left ventricle 66 when aortic valve 62 opens during systole. For clarity of illustration, only a right coronary artery 68 is shown in FIG. 1.

Device 50 typically comprises a hollow longitudinal element 80 and at least one elliptical (e.g., circular) flap 82, typically positioned near a distal end 84 of element 80. Element 80 is shaped so as to define interior region 64 between an inflow opening 86 at a proximal end 88 of element 80, and an outflow opening 90 at distal end 84. Typically, the circumference of element 80 increases from distal end 84 to proximal end 88.

Figure 2A:
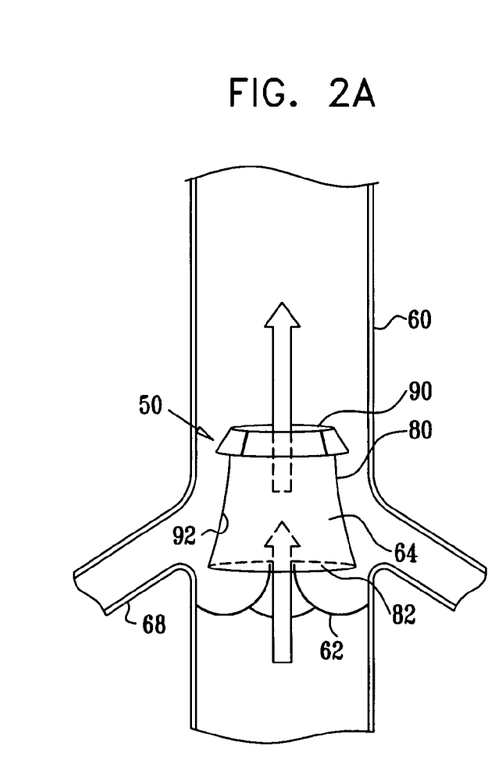
FIGS. 2A-C are schematic illustrations of the amplification device of FIG. 1 during operation, in accordance with an embodiment of the present invention.
Figure 2B:
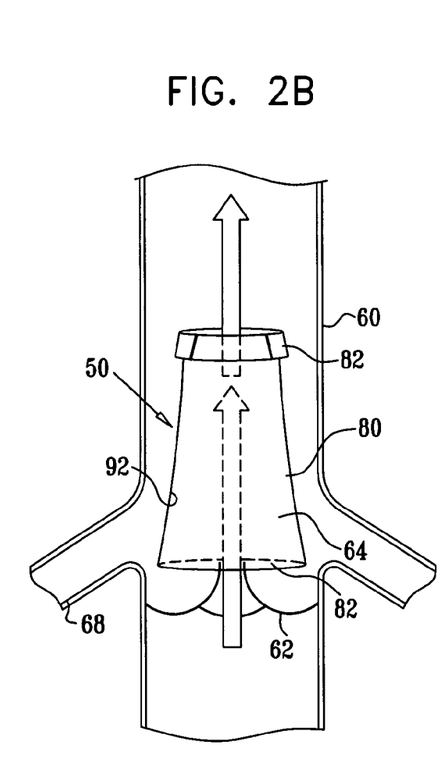

FIGS. 2A-C are schematic illustrations of amplification device 50 during operation, in accordance with an embodiment of the present invention. At the beginning of systole, as shown in FIG. 2A, aortic valve 62 opens, and blood exiting the left ventricle through aortic valve 62 enters interior region 64 of device 50 via inflow opening 82. The blood flows through element 80, and exits interior region 64 via outflow opening 90. The blood passing through element 80 applies work to a surface 92 of element 80, thereby longitudinally expanding the element and storing energy therein. As shown in FIG. 2B, element 80 expands longitudinally as systole continues. As the element expands, flap 82 typically but not necessarily folds down against an external surface of element 80 because of resistance by blood in the aorta.

Figure 2C:
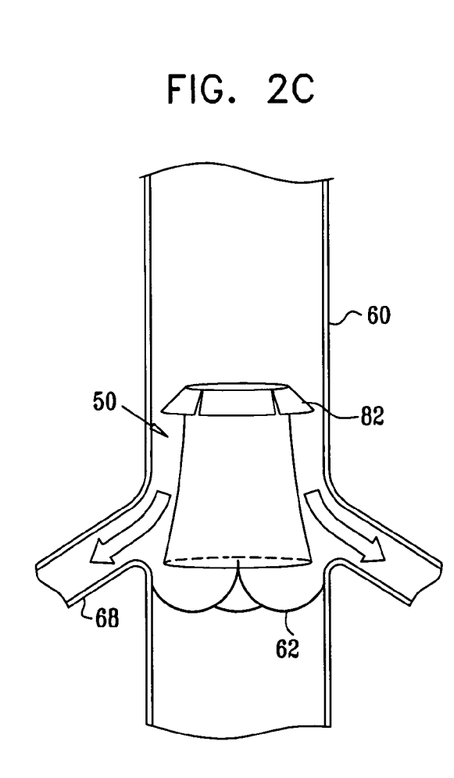

During diastole, as shown in FIG. 2C, the energy stored in element 80 causes the element to contract longitudinally. During the contraction, blood in the aorta causes flap 82 to open away from element 80, such that a lower surface of the open flap pushes blood into the coronary arteries, thereby increasing blood pressure and flow in the coronary arteries. As appropriate, during diastole, flap 82 may be a small distance from the inner wall of aorta 60, or, alternatively, in direct contact therewith.

For some applications, element 80 is elastic, and stores the energy applied thereto by expanding longitudinally. Alternatively or additionally, device 50 comprises at least one spring or other discrete elastic element surrounding, integrated into, or within element 80 (configurations not shown), and longitudinal expansion of the spring stores work applied to surface 92. For some applications, device 50 is adapted to be inserted into aorta 60 and/or held in place therein by coupling the device to an expandable stent similar to those known in the art.

Figure 3:
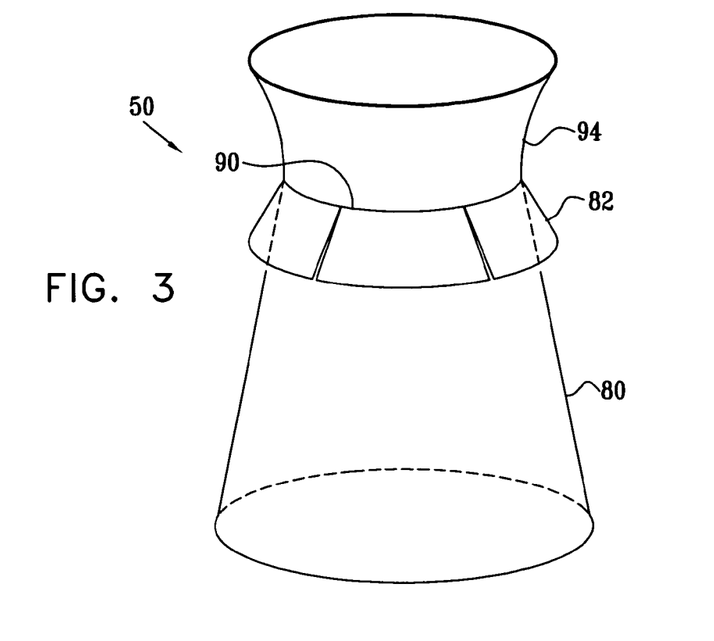
FIGS. 3 and 4 are schematic illustrations of respective configurations of the amplification device of FIG. 1, in accordance with respective embodiments of the present invention.

Reference is made to FIG. 3, which is a schematic illustration of a configuration of extracardiac blood flow amplification device 50, in accordance with an embodiment of the present invention. In this embodiment, amplification device 50 additionally comprises a blood guide element 94 coupled to element 80 at outflow opening 90 thereof. Blood guide element 94 is shaped so as to generally reduce any blood turbulence that may be caused by amplification device 50. For example, blood guide element 94 may be flared, i.e., generally shaped like a bell of a trumpet.

Figure 4:
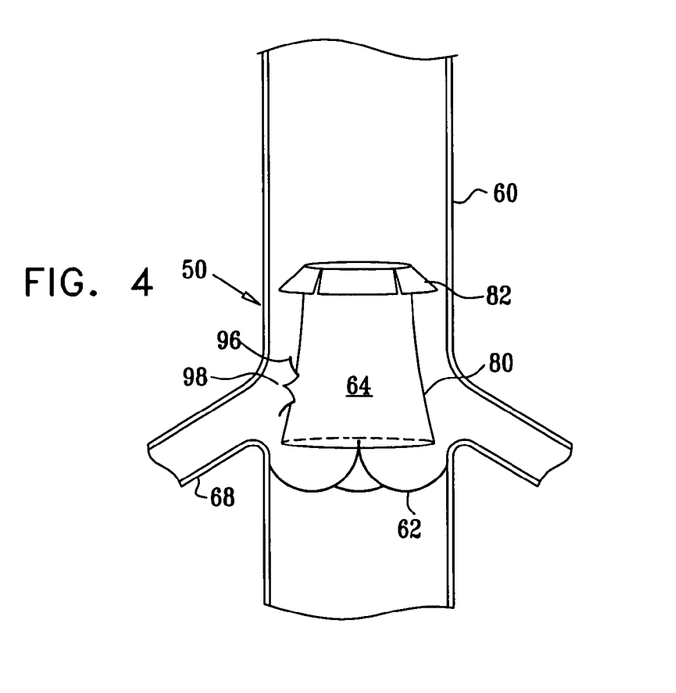

Reference is made to FIG. 4, which is a schematic illustration of another configuration of extracardiac blood flow amplification device 50, in accordance with an embodiment of the present invention. In this embodiment, element 80 of amplification device 50 comprises at least one pressure-sensitive valve 96, which, when open, allows passage of blood from interior region 64 of device 50 to an external region 98 of aorta 60 in a vicinity of the coronary arteries. Valve 96 is configured to remain closed unless the pressure in interior region 64 exceeds the pressure in external region 98. Such a pressure gradient typically does not occur during normal operation of amplification device 50. However, if flap 82 should fail to fold down against the external surface of element 80 during systole, the pressure in external region 98 would drop. As a result, valve 96 would open, allowing fresh oxygenated blood to reach external region 98 and the coronary arteries. For some applications, valve 96 comprises one or more elastic flaps integrated with element 80. Alternatively, valve 90 comprises any appropriate valve known in the art. For some applications, extracardiac blood flow amplification device 50 comprises both valve 96 and blood guide element 94, described hereinabove with reference to FIG. 3.

Figure 5:
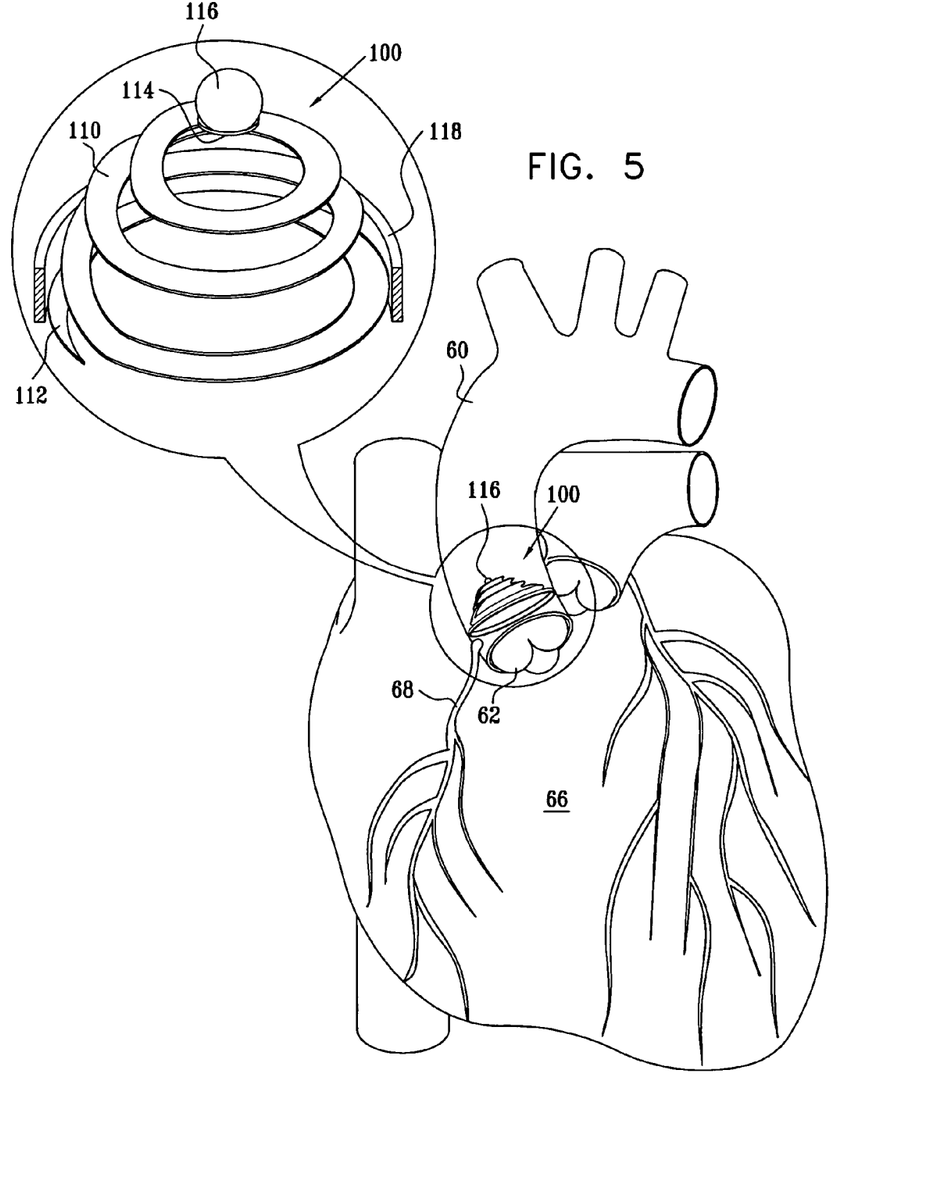
FIG. 5 is a schematic illustration of another extracardiac blood flow amplification device, in accordance with an embodiment of the present invention.

Reference is now made to FIG. 5, which is a schematic illustration of an extracardiac blood flow amplification device 100, in accordance with an embodiment of the present invention. Amplification device 100 is adapted to be implanted in ascending aorta 60 in a vicinity of aortic valve 62, typically above the left and right coronary sinuses. Amplification device 100 comprises a generally helically shaped spring or other elastic element 110, a diameter of which typically decreases from a proximal end 112 (i.e., the end nearer the aortic valve) towards a distal apex 114 thereof. A lower surface of each loop of helical element 110 is typically rounded, e.g., convex towards the heart valve, which generally reduces blood turbulence. For some applications, an upper surface of each loop is also convex.

Helical element 110 typically comprises a weight 116, coupled to apex 112 or integral to the body of the helical element. Weight 116 typically has a mass of between about 1 g and about 10 g, or, for some applications, between about 10 g and about 100 g. Alternatively or additionally, helical element 110 is shaped so as to have between about 1 g and about 10 g (or between about 10 g and about 100 g) of mass distributed throughout all or a portion of the length of the helical element.

The characteristic resonant frequency of helical element 110 is typically between about 65 and about 80 per minute. Alternatively, the frequency is less than 65 per minute or greater than 80 per minute. For some applications, helical element 110 is adapted to be actively or passively configurable to change its resonant frequency based on the heart rate of the subject.

Typically, amplification device 100 comprises an anchoring element 118 coupled to helical element 110 in a vicinity of proximal end 112 thereof. The anchoring element is adapted to secure amplification device 100 to the wall of aorta 60. For example, anchoring element 118 may comprises a stent similar to those known in art for cardiac applications.

Figure 6A:
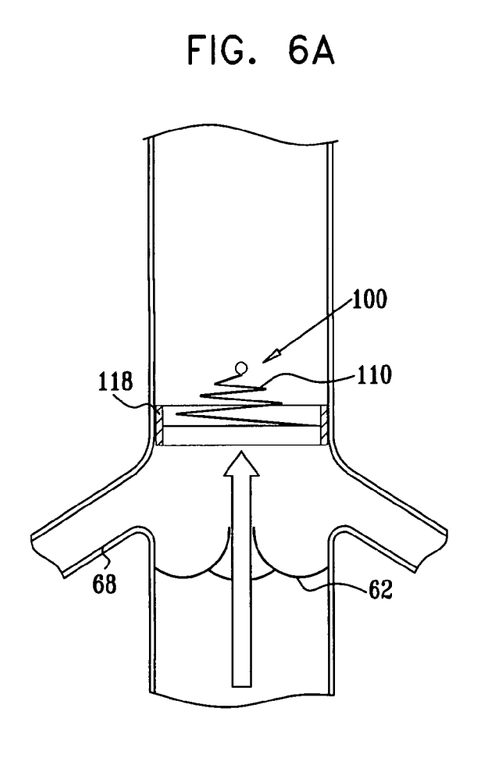
FIGS. 6A-C are schematic side-view illustrations of the amplification device of FIG. 5 during operation, in accordance with an embodiment of the present invention.
Figure 6B:
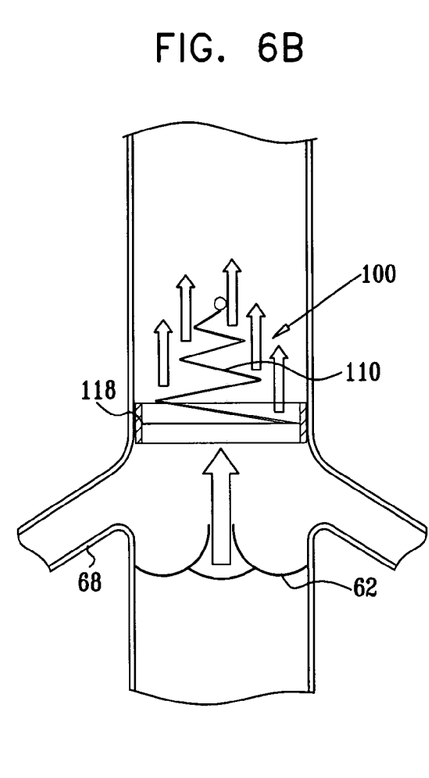
Figure 6C:
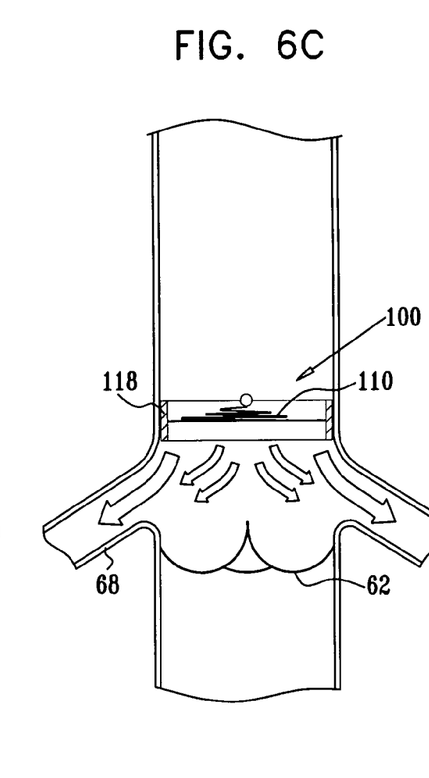

FIGS. 6A-C are schematic side-view illustrations of amplification device 100 during operation, in accordance with an embodiment of the present invention. At the beginning of systole, as shown in FIG. 6A, helical element 110 is in its resting position. Aortic valve 62 opens, and blood exiting the left ventricle through aortic valve 62 flows through helical element 110. The blood applies work to the element, thereby longitudinally expanding the element and storing energy therein. As shown in FIG. 6B, helical element 110 expands longitudinally as systole continues. During diastole, as shown in FIG. 6C, the energy stored in helical element 110 causes the element to contract longitudinally. During the contraction, the element pushes blood towards and into the coronary arteries, thereby increasing blood pressure and flow in the coronary arteries.

Figure 7:
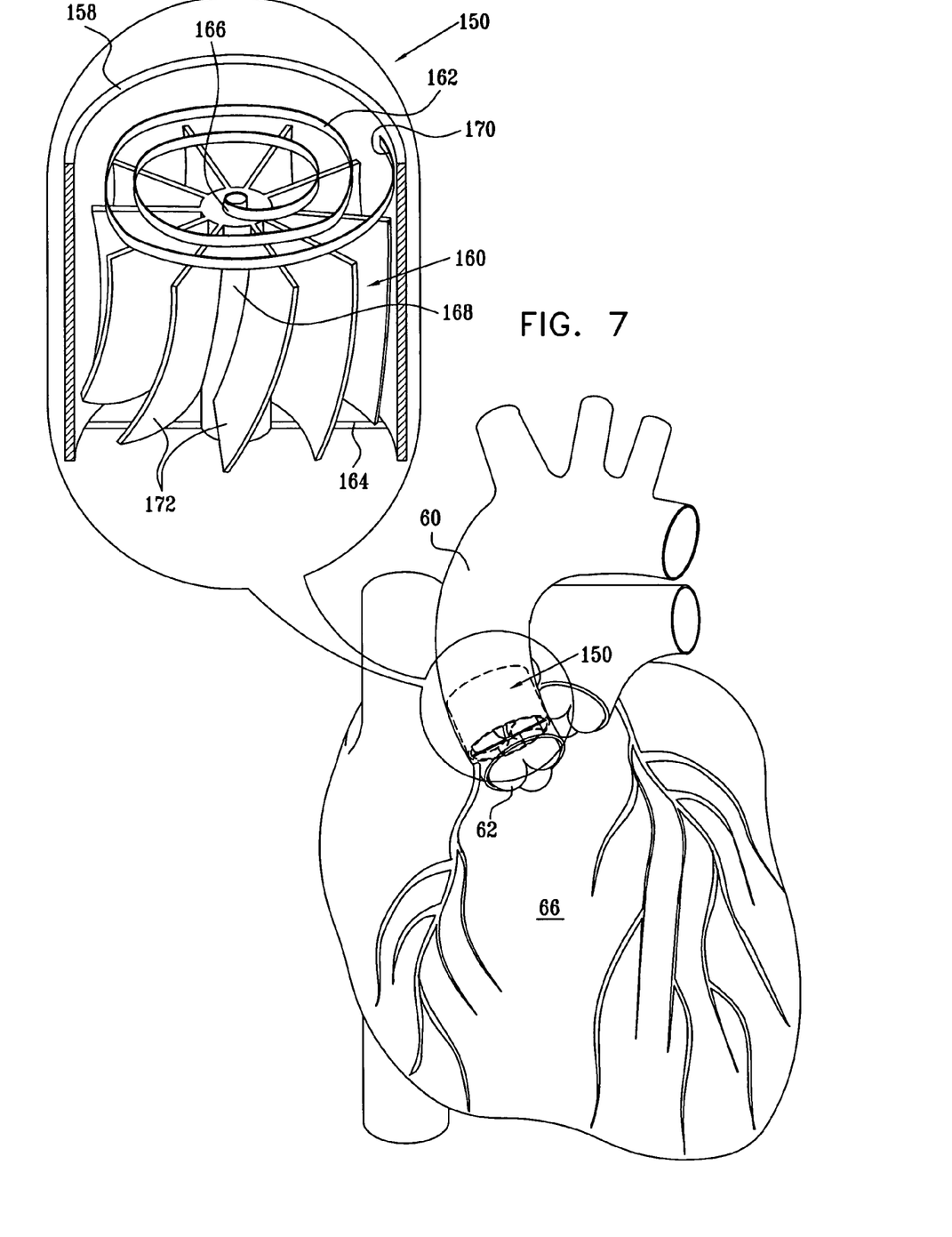
FIG. 7 is a schematic illustration of yet another extracardiac blood flow amplification device, in accordance with an embodiment of the present invention.

Reference is now made to FIG. 7, which is a schematic illustration of an extracardiac blood flow amplification device 150, in accordance with an embodiment of the present invention. Amplification device 150 is adapted to be implanted in ascending aorta 60 in a vicinity of aortic valve 62, typically above the left and right coronary sinuses. Amplification device 150 comprises a cylindrical casing 158, a turbine 160, and an elastic element 162, such as a spring. Turbine 160 is mounted in casing 158, such as by one or more connecting elements 164. For some applications, elastic element 162 comprises a spring having a planar spiral shape, similar to a mechanical watch spring. Typically, an inner end 166 of the spring is coupled to an axial shaft 168 of turbine 160, and an outer end 170 of the spring is coupled to casing 158.

Figure 8A:
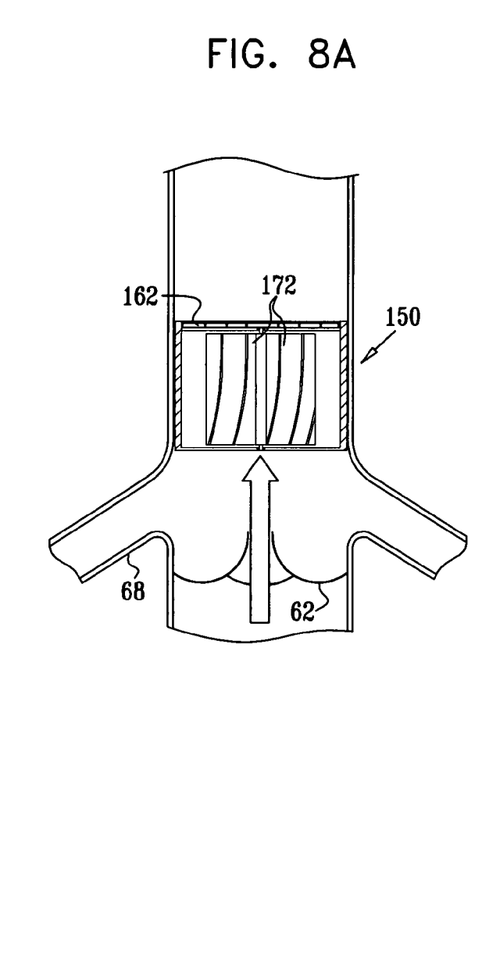
FIGS. 8A-C are schematic illustrations of the amplification device of FIG. 7 during operation, in accordance with an embodiment of the present invention.
Figure 8B:
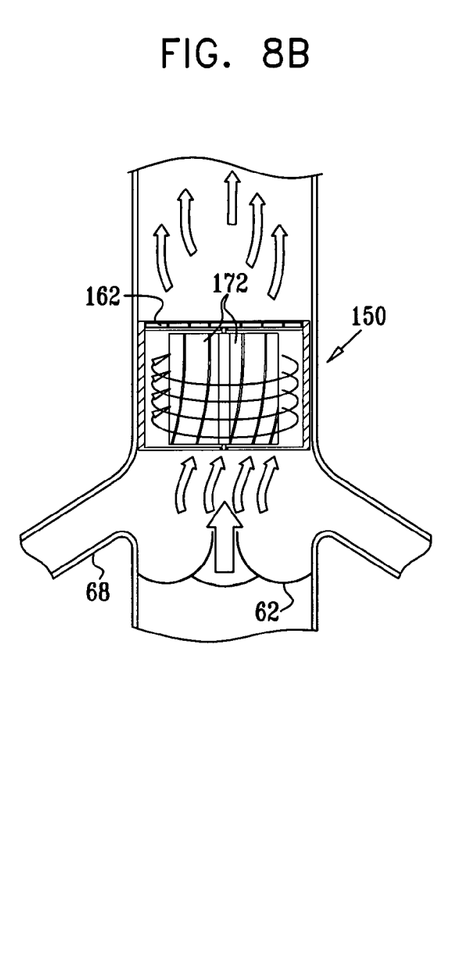
Figure 8C:
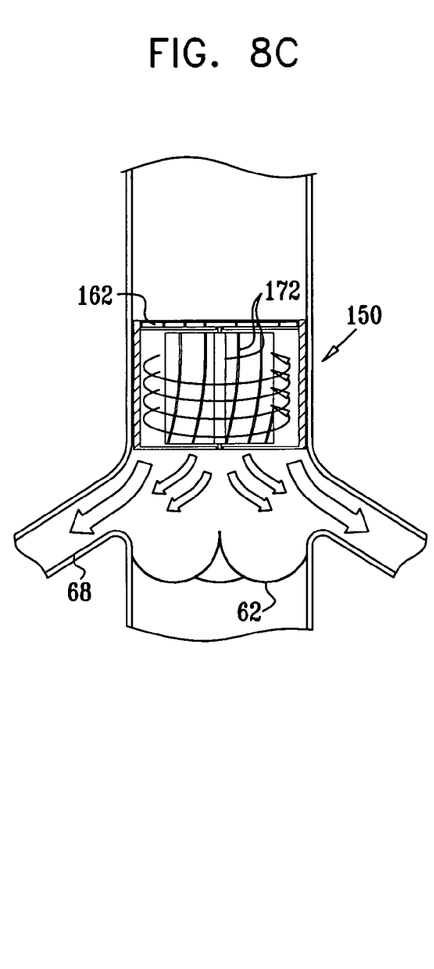

FIGS. 8A-C are schematic illustrations of amplification device 150 during operation, in accordance with an embodiment of the present invention. At the beginning of systole, as shown in FIG. 8A, elastic element 162 is in its resting position. Aortic valve 62 opens, and blood exiting the left ventricle through aortic valve 62 flows through casing 158 and turbine 160. Blood flowing past turbine blades 172 causes turbine 160 to rotate in a first direction (for example, in the configuration shown in FIGS. 8 and 8A-C, clockwise as viewed from above). The rotation of turbine 160 applies work to elastic element 162, thereby storing energy therein. As shown in FIG. 8C, during diastole, the energy stored in elastic element 162 causes turbine 160 to rotate in a second direction opposite the first direction (e.g., counterclockwise, in the configuration shown in FIGS. 8 and 8A-C). This rotation causes blades 172 to push blood towards and into the coronary arteries, thereby increasing blood pressure and flow in the coronary arteries.

Figure 9:
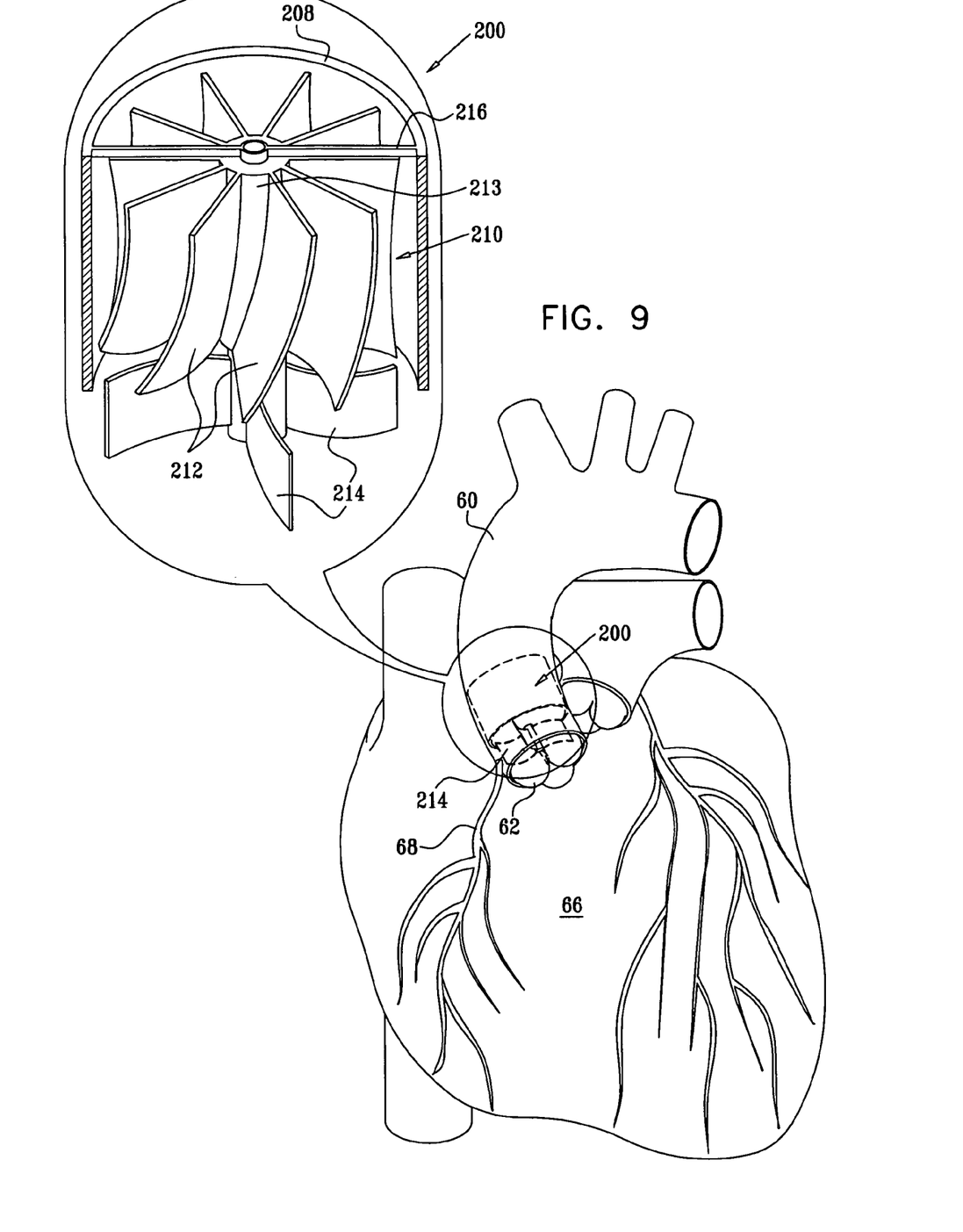
FIG. 9 is a schematic illustration of still another extracardiac blood flow amplification device, in accordance with an embodiment of the present invention.

Reference is now made to FIG. 9, which is a schematic illustration of an extracardiac blood flow amplification device 200, in accordance with an embodiment of the present invention. Amplification device 200 is adapted to be implanted in ascending aorta 60 in a vicinity of aortic valve 62, typically above the left and right coronary sinuses. Amplification device 150 comprises a cylindrical casing 208; a turbine 210, which comprises a plurality of turbine blades 212 coupled to an axial shaft 213; and one or more lower elements 214, such as blades, coupled to a proximal end of turbine 210 (i.e., the end nearer the aortic valve). Turbine 160 is mounted in casing 208, such as by one or more connecting elements 216. For some applications, lower elements 214 are coupled to a proximal end of shaft 213 of turbine 210. Alternatively or additionally, the lower elements are coupled to proximal ends of respective turbine blades 212 (configuration not shown).

During systole, aortic valve 62 opens, and blood exiting the left ventricle through aortic valve 62 flows through casing 208 and turbine 210. Blood flowing past turbine blades 212 during systole causes turbine 210 to rotate, thereby rotating lower elements 214. The movement of lower elements 214 pushes blood towards the periphery of aorta 60, and thus towards and into the coronary arteries, thereby increasing blood pressure and flow in the coronary arteries. For some applications, turbine 160 continues rotating during at least a portion of diastole, thereby continuing to cause lower elements 214 to push blood towards and into the coronary arteries during such portion of diastole.

Figure 10:
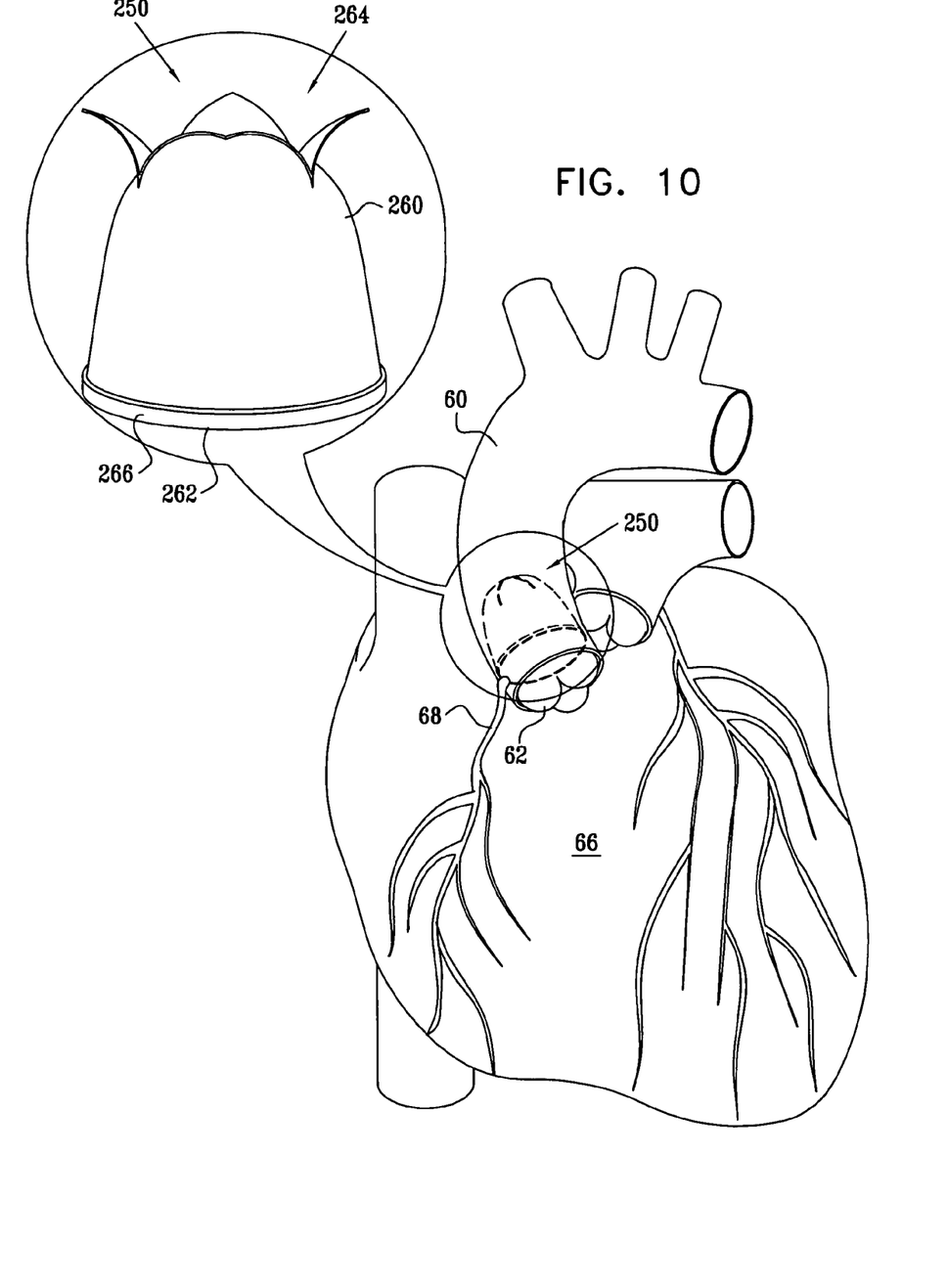
FIG. 10 is a schematic illustration of another extracardiac blood flow amplification device, in accordance with an embodiment of the present invention.

Reference is now made to FIG. 10, which is a schematic illustration of an extracardiac blood flow amplification device 250, in accordance with an embodiment of the present invention. Amplification device 250 is adapted to be implanted in ascending aorta 60 in a vicinity of aortic valve 62, typically above the left and right coronary sinuses. Amplification device 250 comprises a generally dome-shaped elastic cup element 260, shaped so as to define an opening 262 at a proximal end thereof. At a distal end thereof, cup element 260 comprises a valve 264. For some applications, valve 264 comprises one or more elastic flaps integrated with cup element 260. For example, valve 264 may be formed as an X-shaped cut in cup element 260, similar to the opening in the nipple of some infant bottles. Alternatively, valve 264 comprises any appropriate valve known in the art. Typically, amplification device 250 comprises an anchoring element 266, adapted to secure amplification device 250 to the wall of aorta 60, such that all or substantially all blood flowing from aortic valve 62 enters cup element 260. For example, anchoring element 266 may comprise a stent similar to those known in art for cardiac applications.

Figure 11A:
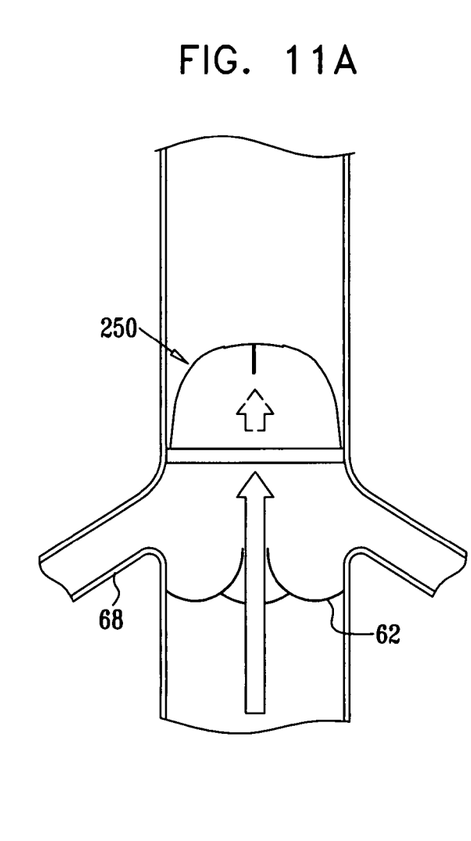
FIGS. 11A-F are schematic illustrations of the amplification device of FIG. 10 during operation, in accordance with an embodiment of the present invention.
Figure 11B:
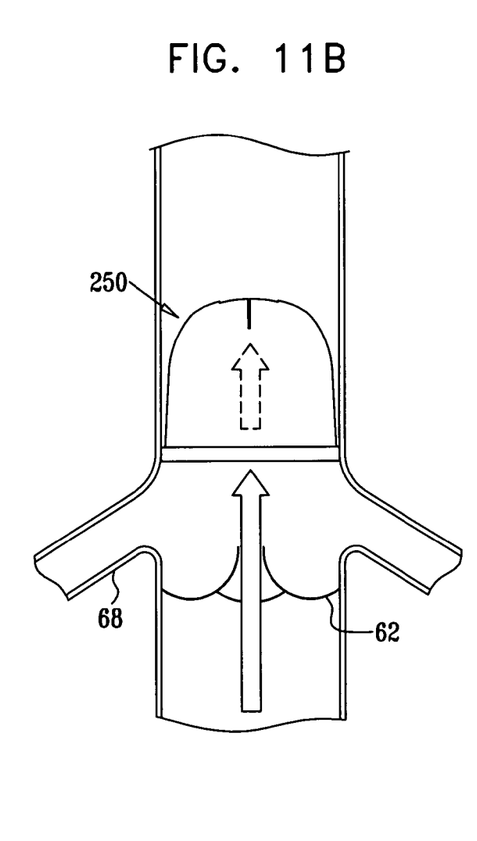
Figure 11C:
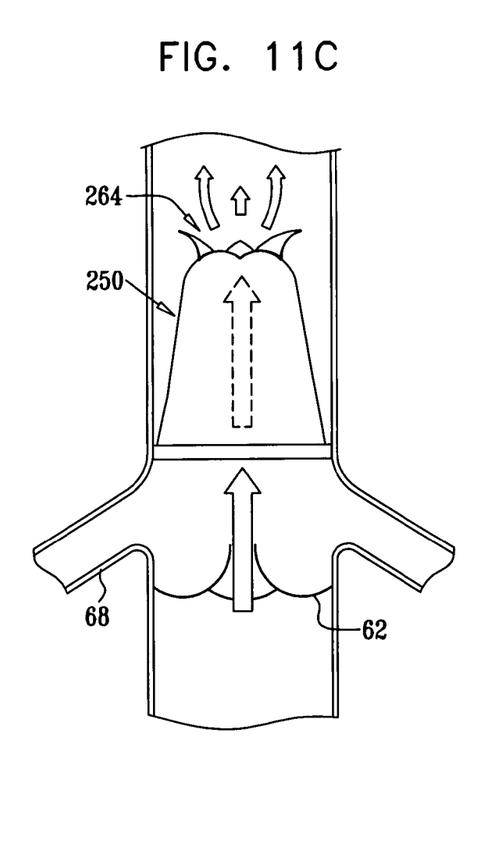
Figure 11D:
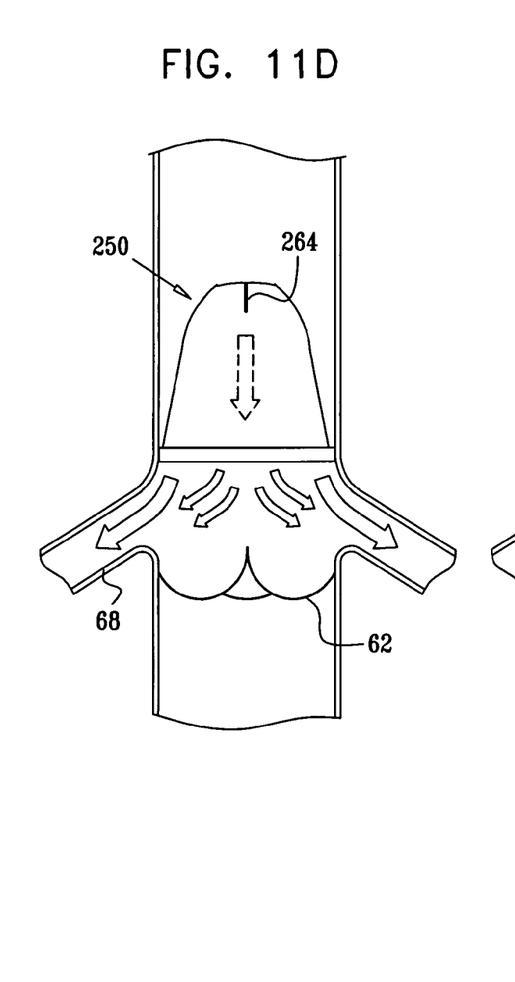
Figure 11E:
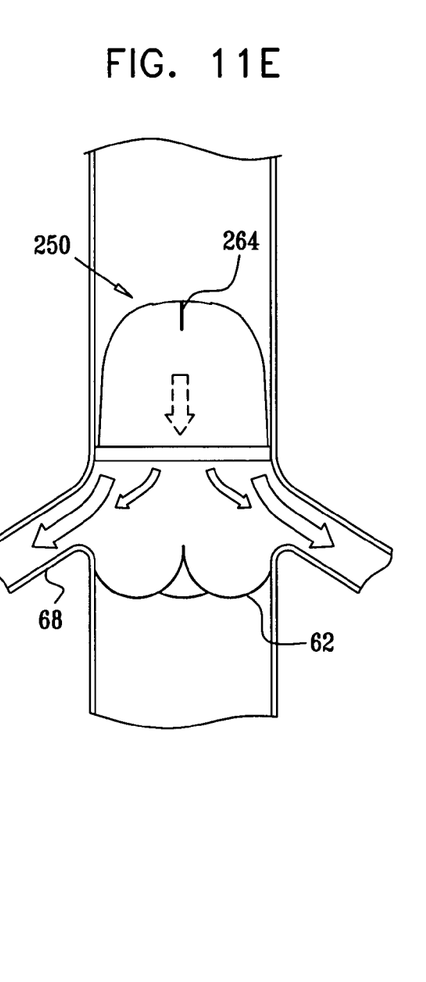
Figure 11F:
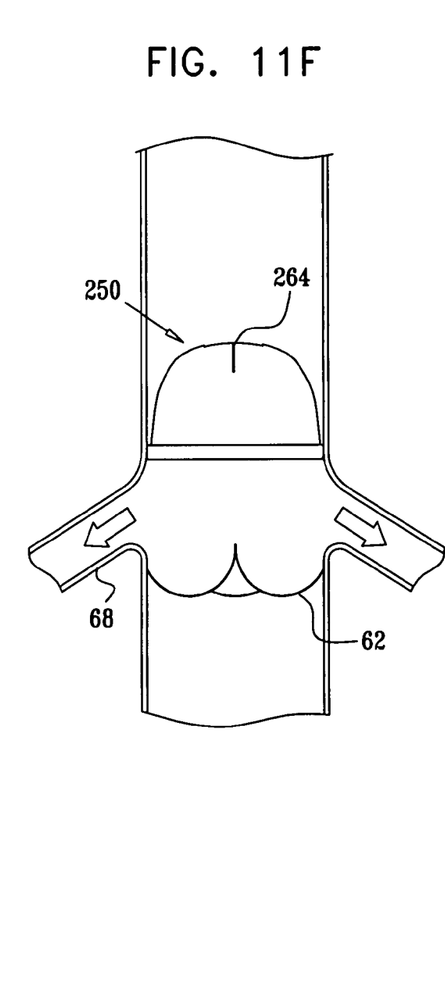

FIGS. 11A-F are schematic illustrations of amplification device 250 during operation, in accordance with an embodiment of the present invention. At the beginning of systole, as shown in FIG. 11A, cup element 260 is in its most contracted, resting position. Aortic valve 62 opens, and blood exiting the left ventricle through aortic valve 62 enters cup element 260. The blood applies work to the flexible wall of the cup element, causing the cup element to expand longitudinally and store energy in the wall thereof, as shown in FIG. 11B. As systole continues, the blood pressure in cup element 260 continues to increase, until a sufficient pressure gradient causes valve 264 to open, allowing blood to pass through amplification device 250 into ascending aorta 60. As the blood pressure within cup element 260 drops during diastole, valve 264 closes, as shown in FIG. 11D. The energy stored in cup element 260 causes the cup element to contract longitudinally, as shown in FIG. 11E and 11F. During the contraction, the cup element pushes blood towards and into the coronary arteries, thereby increasing blood pressure and flow in the coronary arteries.

Figure 12:
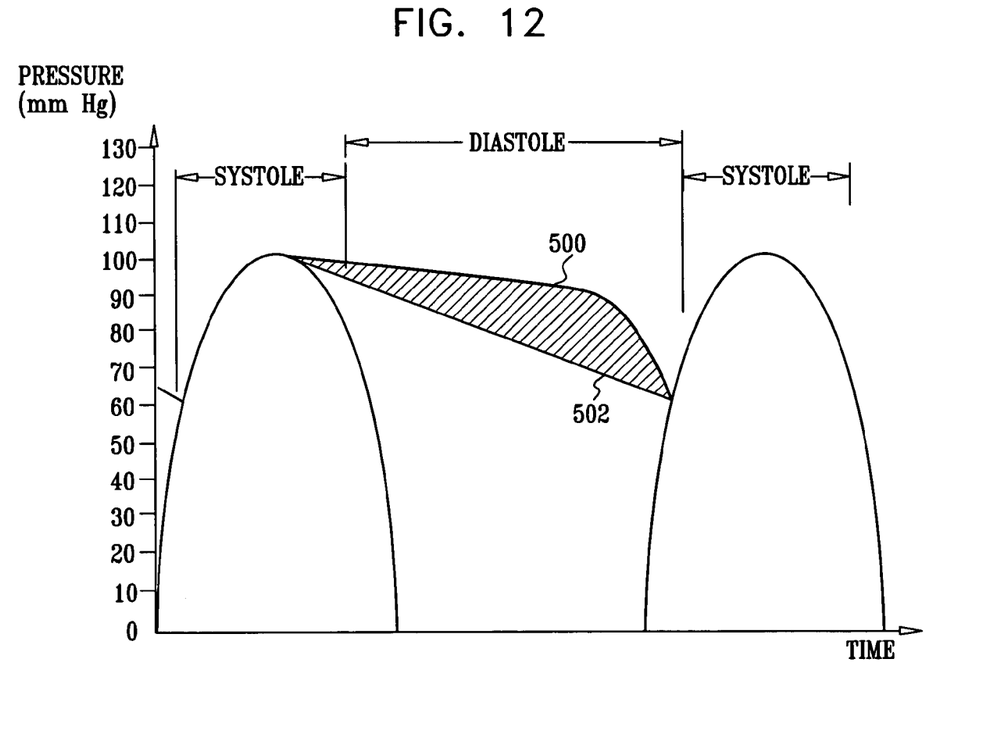
FIG. 12 is a graph showing example pressure curves without treatment and during treatment with the amplification devices of FIGS. 1, 5, 7, 9, and 10, in accordance with an embodiment of the present invention.

FIG. 12 is a graph showing example pressure curves without treatment and during treatment with amplification devices 50, 100, 150, 200, and 250, in accordance with an embodiment of the present invention. It is emphasized that these pressure curves are exemplary, and reflect assumptions regarding a particular configuration of the amplification devices and a theoretical subject's reactions to the devices. In actual human use, physiological responses are expected to vary substantially from subject to subject, in part dependent upon the particular configuration of the devices.

A curve 502 represents blood pressure in a portion of at least one coronary artery without treatment with one of the amplification devices. A curve 500 represents blood pressure in the portion of the coronary artery during treatment with the device. As can be seen, during most of diastole, the device supplies blood to the coronary arteries at substantially higher pressure than would be provided without use of the device.

In an embodiment of the present invention, some or all of the extracardiac blood flow amplification devices described hereinabove are adapted to be implanted at a site in the body downstream from the ascending aorta in a vicinity of the aortic valve (e.g., a site in the ascending aorta remote from the aortic valve, a descending aortic site, or a femoral artery site), such that energy is stored during systole and released during diastole, in order to increase diastolic pressure in a coronary artery.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus, comprising:
    a passive rotating device,
        configured to be implanted in an artery of a subject,
        comprising an axial shaft and one or more blades coupled to the shaft, configured to rotate due to blood passing through the rotating device during systole applying work to the blades, and
        configured to push blood towards an artery of the subject other than the artery in which the apparatus is implanted, in response to the blood applying work to the blades; and
    a casing, configured to couple the rotating device to the artery.

2. The apparatus according to claim 1, wherein the passive rotating device is configured to be implanted in an aorta of the subject.

3. The apparatus according to claim 1, wherein the passive rotating device is configured to be implanted in the artery of the subject by aligning the axis of the rotating device with an axis of the artery.

4. The apparatus according to claim 1, wherein in pushing blood towards the artery of the subject other than the artery in which the apparatus is implanted, the passive rotating device is configured to push the blood towards a periphery of the artery in which the apparatus is implanted.

5. The apparatus according to claim 1, wherein the passive rotating device is configured to push blood towards the artery of the subject other than the artery in which the apparatus is implanted, during at least a portion of diastole.

6. The apparatus according to claim 1, wherein the passive rotating device is configured to be implanted in an aorta of the subject, and wherein in pushing blood towards the artery of the subject other than the artery in which the apparatus is implanted, the passive rotating device is configured to push the blood into a coronary artery of the subject.

7. Blood-flow energy storage apparatus comprising:
    an always-open blood-flow pathway portion arranged to be implanted in a blood vessel of a subject; and
    a displaceable blood-flow energy storage portion:
        at least partially located within the always-open blood-flow pathway portion and being displaceable in response to blood flow through the energy storage portion, for receiving kinetic energy from the blood flow and temporarily storing the kinetic energy, and
        comprising a turbine, comprising an axial shaft and one or more turbine blades coupled to the shaft, the turbine rotating in a first direction in response to blood flow therethrough.

8. The apparatus according to claim 7, wherein the blood-flow energy storage portion further comprises an elastic element, coupled to the turbine, the turbine storing the kinetic energy from the blood flow by storing the energy in the elastic element, and the elastic element releasing the stored energy by rotating the turbine in a second direction opposite the first direction.

9. The apparatus according to claim 8, wherein the turbine is rotated by the blood flow therethrough during systole of the subject, and wherein the elastic element drives the blades to push blood towards at least one coronary artery of the subject by rotating the turbine in the second direction during diastole of the subject.

* * * * *